United States Patent
VanDahm et al.

(10) Patent No.: US 6,342,641 B1
(45) Date of Patent: Jan. 29, 2002

(54) PURIFIED BISPHENOL A ETHOXYLATES AND PROCESSES OF PURIFYING THEREOF

(75) Inventors: Richard Allan VanDahm, Spartanburg; Ricky Lee Ritz, Inman, both of SC (US)

(73) Assignee: Milliken & Company

( * ) Notice: Subject to any disclaimer, the term of this patent is extended or adjusted under 35 U.S.C. 154(b) by 0 days.

(21) Appl. No.: 09/568,072

(22) Filed: May 10, 2000

(51) Int. Cl.⁷ .............................................. C07C 43/253
(52) U.S. Cl. ......................... 568/609; 528/87; 568/608
(58) Field of Search ................................ 568/608, 609; 528/87

(56) References Cited

U.S. PATENT DOCUMENTS 4,029,879 A * 6/1977 Muzzio ........................ 536/4
4,306,943 A * 12/1981 Mori et al. .................... 203/29

* cited by examiner

*Primary Examiner*—Gary Geist
*Assistant Examiner*—Zachary C. Tucker
(74) *Attorney, Agent, or Firm*—Terry T. Moyer; William S. Parks

(57) ABSTRACT

Purified bisphenol A ethoxylates are provided which are produced through the base-catalyzed addition of ethylene oxide to a bisphenol A. The purification step involves the neutralization with a mineral acid (namely phosphoric acid) and subsequent treatment with a colloidal metal silicate. The neutralization step removes substantially all of the excess cation (or salt) of the base catalyst to produce a uniformly low salt content bisphenol A ethoxylate. Such a low-salt product is thus easy to produce in continuously high yields. The process itself is also encompassed within this invention.

8 Claims, No Drawings

PURIFIED BISPHENOL A ETHOXYLATES AND PROCESSES OF PURIFYING THEREOF

FIELD OF THE INVENTION

This invention relates to purified bisphenol A ethoxylates produced through the base-catalyzed addition of ethylene oxide to bisphenol A. The purification step involves the neutralization with a mineral acid (namely phosphoric acid) and the subsequent treatment with a colloidal metal silicate. The neutralization step removes substantially all of the excess cation (or salt) of the base catalyst to produce a uniformly low salt content bisphenol A ethoxylate. Such a low-salt product is thus easy to produce in continuously high yields. The process itself is also encompassed within this invention.

BACKGROUND OF THE PRIOR ART

Bisphenol ethoxylates are useful as monomers and additives in a wide variety of different areas, including, without limitation, as monomers for epoxy, polyester and polyurethane resins and reactive diluents in high solids coatings. However, problems have arisen in the past due to the presence of excess salts and/or cations which remain within the resultant solution after catalysis of the reaction of ethylene oxide with the bisphenol A starting material. The catalysts employed are generally strong bases (such as, primarily, potassium hydroxide, sodium hydroxide, and the like) which provide high reactivity and are easy to use. Unfortunately, the presence of residual catalyst in the final product often interferes with the subsequent use of the bisphenol A ethoxylate, and thus the basic catalyst must be removed in order to provide the desired final product.

In the past, a variety of methods have been claimed for the removal of catalyst residues from the products obtained through the base catalyzed reaction of alcohols and phenols with ethylene oxide and propylene oxide (polyether polyols). The most widely used method involves neutralization by the addition of low pH mineral acids (such as hydrochloric acid, sulfiric acid, and the like) in amounts sufficient to convert the catalyst to insoluble salt (with the base catalyst cation) and water (with the hydroxide of the catalyst and the hydrogen of the acid) which could then be removed by filtration. In the past, there was no way to precisely control the actual amount of salt that would be removed by this method. This method for salt removal is highly dependent on the pH after neutralization, the type and size of salt crystal formed, water content during filtration and the filter media used. While the majority of the salts may be removed by filtration, there often remains a residual amount of salt which is dissolved in the filtrate or is of insufficient particle size to be retained by the filter media. While this process may be adequate at reducing the residual salt to a level acceptable for some applications, it does not afford a means of consistently achieving residual salt levels low enough for more demanding applications. In this case further neutralization and/or removal steps would be required (which adds an extra process step to an already costly method), or the end user is forced to rely on a nonuniform production method from the polyether polyol producer.

Another means of removing the alkaline ethoxylation catalyst (U.S. Pat. No. 5344996) employs the use of acid clays such as alumina, montmorillonite, magnesium silicate, etc. which are insoluble in the polyether polyol, to act as an absorbent for the catalyst. The insoluble magnesium silicate along with the absorbed catalyst is then removed by filtration. There are several drawbacks to this method. Typically, one is required to use the synthetic magnesium silicate at a level of around 5 to 10 times the residual catalyst amount. This results in a substantial amount of filtration solids which must be disposed of by landfill or incineration. In addition, the residual solids from filtration, if not protected from exposure to air, can ignite. Handling large amounts of a potential ignition source is less than desirable in areas where ethylene oxide is in use. Finally, the results of this method are also subject to variation depending on water levels present at filtration, the time and temperature during the absorption process and the efficiency of filtration.

Methods of catalyst removal have also been described (DE 4336923JP 05085980) which involve neutralization of the alkaline catalyst by passing carbon dioxide through the crude reaction mixture and then removing the precipitated carbonate by filtration. This method suffers from many of the same drawbacks as the previous described mineral acid neutralization procedure and may also require multiple treatments to attain reasonably low residual catalyst levels. Others have described catalyst removal (WO 9620972, DE 3016112) by washing the polyether polyol with water at an elevated temperature and then passing the mixture through a coalescence medium to separate the water/catalyst solution from the polyol. In order for this procedure to work effectively, the polyether polyol must have a limited solubility in water at the separation temperature. The requirement precludes the use of this procedure on polyols having a high polyethylene oxide content.

To combat the difficulties and inconsistencies of the above approaches, some alternate methods were developed to provide polyether polyols of low salt content. Such a process is disclosed within German Patent 3,229,216, which requires the combined steps of a phosphoric acid neutralization together with a magnesium silicate adsorption of the base-catalyzed reaction product of a polyol and a combination of propylene oxide and ethylene oxide. After filtration of the resultant salts from the liquid solution, the excess water is then stripped (through heating) and the remaining liquid is the desired ethoxylated polyol. Such a procedure does aid in efficiency through a one-step neutralization/adsorption method and appears to afford a lower and more consistent level of residual salt in the final product. However, the products were produced using mostly, and in some cases exclusively, propylene oxide. Materials of this type which have a high propylene oxide content are known to be far less water sensitive than those with a high ethylene oxide content and have a diminished capacity to dissolve inorganic salts. Nowhere in this patent is it demonstrated that the disclosed process is effective at removal of residual salts from materials with high ethylene oxide content. In addition, using this method, there is still a substantial amount of solid generated from filtration that can only be disposed of by incineration or in a landfill and since it contains the magnesium silicate the potential for ignition of this solid exists. In addition, this procedure is carried out in the presence of approximately 1 percent water. In order to provide an acceptable product for most applications, the filtrate must be recharged to the reactor and the water removed to an acceptable level.

There is thus a need to provide a procedure that produces a consistently low salt-content polyol ethoxylates and specifically ethoxylates of bisphenol A, that does not produce large amounts of waste solids that must be either incinerated or disposed of in a landfill and which presents less of a ignition hazard. To date, no such consistent procedure has been developed, disclosed, or accorded this industry within the pertinent prior art.

OBJECTS AND DESCRIPTION OF THE INVENTION

It is thus an object of the invention to provide a process for the production of a low salt content bisphenol A ethoxylate wherein such process consistently produces a salt content of below 7 parts per million of salt within the resultant ethoxylate. A further object of the invention is to provide a relatively inexpensive method of achieving such low salt levels. Yet another object of this invention is to provide a low salt content bisphenol A ethoxylate for utilization in the manufacture of spandex fiber.

Accordingly, this invention encompasses a method of producing a bisphenol A ethoxylate comprising the sequential steps of (a) reacting ethylene oxide with bisphenol A in the presence of a base catalyst to produce a bisphenol A ethoxylate;

(b) neutralizing said bisphenol A ethoxylate with a mineral acid;

(c) heating said neutralized bisphenol A ethoxylate to remove substantially all of the residual water;

(d) circulating the neutralized bisphenol A ethoxylate through a filter to remove any resultant insoluble salts;

(e) adding a magnesium silicate to said neutralized, filtered bisphenol A ethoxylate of step "d"; and (f) refiltering the resultant composition of step "e" to remove the magnesium silicate and absorbed catalyst.

This invention also concerns a bisphenol A ethoxylates possessing a salt content of less than 7 ppm produced by the method above. Nowhere within the pertinent prior art has such a specific method or product made by such a method been disclosed or fairly suggested. As noted above, the closest art, German Patent 3,229,216, discloses a polyol ethoxylate produced through the simultaneous performance of neutralization and adsorption. Such a procedure results in the production of batches exhibiting diminished salt contents but pertains to products which contain either propylene oxide exclusively or as a majority (>75%) constituent and leads to the generation of large amounts of solid waste which must be disposed of either in a landfill or by incineration. The present invention, through the separation of such neutralization and adsorption steps and removal of water prior to filtration, alleviates such problems and provides highly desired consistent and low salt contents for the resultant bisphenol A ethoxylates. As such, the current invention is a surprisingly effective improvement over the pertinent prior art.

The particular acid neutralizer present within this inventive process is a mineral aid, such as hydrochloric acid, phosphoric acid, sulfuric acid, and the like, that effectively neutralizes the base catalyst to form a salt and water. The use of a mineral acid is preferred since the reaction with the residual catalyst generates inorganic salts which are far less soluble in the bisphenol A etloxylate than organic salts. Preferably, such an acid is phosphoric acid. The use of hydrochloric acid can lead to corrosion of processing equipment and the use sulfiric acid can, in some instances, lead to the formation of undesired color in the bisphenol A ethoxylate. Thus, the base catalyst is generally an alkali or alkaline earth hydroxide or oxide. Compounds such as potassium hydroxide, sodium hydroxide, calcium hydroxide, and the like, are thus preferred with potassium hydroxide the most preferred. The metal silicate compound may comprise any of a number of both natural and synthetic silicates such as aluminum silicate, bentonite, montmorillonite, calcium silicate, magnesium silicate and the like. Preferably, this silicate is magnesium silicate.

Any molar amount of alkylene oxide, may be utilized to ethoxylate the bisphenol A within the inventive process. Preferably, this molar amount is from about 2 to about 30; more preferably from about 2 to about 10; and most preferably about 6. The base catalyst is preferably present in very low amounts in relation to the polyether alcohol and the ethylene oxide; thus, a range of from about 0.05 to about 0.2 grams per grams of bisphenol may be utilized; preferably this range is from 0.08 to about 0.15; most preferably from about 0.10 to 0.12. The mineral acid should be added in an amount sufficient to neutralize substantially all of the excess base catalyst and lower the pH of the resultant composition to between 5 and 8, preferably between 5 and 6. Water is produced during the neutralization step and thus needs to be removed from the bisphenol A ethoxylate. A heating step is thus preferred to strip the water from the resultant ethoxylate. The temperature necessary to effectuate such a removal is generally above the boiling point of water with a maximum of roughly 180° C.; about 105 to about 115° is preffered; about 110° is most preferred for this step. In addition, either vacuum or an inert gas sparge, or both may be utilized to facilitate water remova. The metal silicate should be added in very low amounts in order to complex with and remove the remaining cationic species (and possible salts) from the liquid solution. Thus, amounts of from about 0.1 grams to about 1 gram per 100 grams of ethoxylate are desired; 0.1 to about 0.8 grams are preferred; 0.2 most preferred.

PREFERRED EMBODIMENTS OF THE INVENTION

The invention is more particularly defined by the following non-limiting examples:

EXAMPLE 1

2794 grams of a six mole ethoxylate of bisphenol A was prepared through reaction of 1286 grams of bisphenol A with 1508 grams of ethylene oxide in the presence of 1.3 grams of potassium hydroxide catalyst at 145° C. The resultant composition was liquid and exhibited a potassium content of 325 parts per million.

EXAMPLE 2

500 grams of the bisphenol A ethoxylate prepared in example 1 was heated to 120° C. under nitrogen and neutralized with a mixture of 1 part 85% phosphoric acid in 3 parts water to a pH of about 5.5. A total of about 1.8 grams of the acid/water mixture was required. The resultant mixture was then heated to about 110° C. under a vacuum with a nitrogen sparge until the remaining water content was below about 0.05% (i.e., substantially all of the water was removed; such a level may be as high as about 0.5%; preferably 0%, but nearly impossible to attain). The resultant liquid was then filtered with a 1 micron filter in order to remove excess neutralized catalyst. The filtrate exhibited a potassium content of about 13 ppm.

EXAMPLE 3

500 grams of the bisphenol A ethoxylate prepared in Example 2 was heated to 120° C. under nitrogen. 1.0 gram of synthetic magnesium silicate (such as Magnesol HMR LS, available from The Dallas Group) was then added and the mixture was heated, with stirring, at 120° C., under a nitrogen purge, for about 2 hours. The remaining magnsium silicate was then removed by filtration with a 1 micron filter at 120° C. The resultant liquid filtrate (bisphenol A ethoxylate) exhibited a potassium content of 0.3 ppm.

EXAMPLE 4 (COMPARATIVE)

500 grams of the bisphenol A ethoxylate prepared in Example 1 was heated to 120° C. under nitrogen and neutralized with a mixture of 1 part 85% phosphoric acid and 3 parts water to a pH of about 5.5. A total of about 1.8 grams of the acid/water mixture was required. Sufficient water was then added to bring the total water content to 1.0%. 1.0 grams of synthetic magnesium silicate (such as Magnesol HM RLS, available from The Dallas Group) was then added and the mixture was heated, with stirring, at 120° C., under a nitrogen purge, for about 2 hours. The remaining magnsium silicate was then removed by filtration with a 1 micron filter at 120° C. The residual water was then removed under vacuum until the residual water content was below 0.05% The resultant liquid filtrate (bisphenol A ethoxylate) exhibited a potassium content of 5.7 ppm.

There are, of course, many alternative embodiments and modifications of the present invention which are intended to be included within the spirit and scope of the following claims.

What we claim is:

1. A method of producing a bisphenol A ethoxylate comprising the sequential steps of
   (a) reacting ethylene oxide with bisphenol A in the presence of a base catalyst to produce a bisphenol A ethoxylate;
   (b) neutralizing said bisphenol A ethoxylate with a mineral acid;
   (c) heating said neutralized bisphenol A ethoxylate to remove substantially all of the residual water;
   (d) circulating the neutralized bisphenol A ethoxylate through a filter to remove insoluble salts;
   (e) adding a metal silicate to said neutralized, filtered bisphenol A ethoxylate of step "d"; and
   (f) refiltering to remove the metal silicate and absorbed catalyst.

2. A liquid solution comprising a bisphenol A ethoxylate exhibiting a salt content of below 7 ppm, wherein said bisphenol A ethoxylate is produced in accordance with the method of claim 1.

3. The method of claim 1 wherein said metal silicate is selected from at least one silicate of the group consisting of natural silicates and synthetic silicates.

4. The method of claim 3 wherein said metal silicate is at least one synthetic silicate.

5. The method of claim 4 wherein said at least one synthetic silicate is magnesium silicate.

6. A liquid solution comprising a bisphenol A ethoxylate exhibiting a salt content of below 7 ppm, wherein said bisphenol A ethoxylate is produced in accordance with the method of claim 3.

7. A liquid solution comprising a bisphenol A ethoxylate exhibiting a salt content of below 7 ppm, wherein said bisphenol A ethoxylate is produced in accordance with the method of claim 4.

8. A liquid solution comprising a bisphenol A ethoxylate exhibiting a salt content of below 7 ppm, wherein said bisphenol A ethoxylate is produced in accordance with the method of claim 5.

\* \* \* \* \*